US 8,889,104 B2

(12) United States Patent
Wiedmann et al.

(10) Patent No.: US 8,889,104 B2
(45) Date of Patent: Nov. 18, 2014

(54) METHOD OF NEUTRALIZING AN AEROSOL CONTAINING A COMPOUND OF INTEREST DISSOLVED IN A LOW PH SOLUTION

(71) Applicants: Timothy S. Wiedmann, Minneapolis, MN (US); Amir A. Naqwi, Eden Prairie, MN (US); Lawrence S. Zisman, Slingerlands, NY (US)

(72) Inventors: Timothy S. Wiedmann, Minneapolis, MN (US); Amir A. Naqwi, Eden Prairie, MN (US); Lawrence S. Zisman, Slingerlands, NY (US)

( * ) Notice: Subject to any disclaimer, the term of this patent is extended or adjusted under 35 U.S.C. 154(b) by 0 days.

(21) Appl. No.: 13/689,812

(22) Filed: Nov. 30, 2012

(65) Prior Publication Data

US 2013/0136702 A1 May 30, 2013

Related U.S. Application Data

(60) Provisional application No. 61/565,057, filed on Nov. 30, 2011.

(51) Int. Cl.
| | |
|---|---|
| *A61M 11/00* | (2006.01) |
| *A61K 9/12* | (2006.01) |
| *A63F 11/00* | (2006.01) |
| *A63F 1/12* | (2006.01) |
| *A61K 9/48* | (2006.01) |
| *G07F 17/32* | (2006.01) |
| *A61K 9/20* | (2006.01) |
| *A63F 1/14* | (2006.01) |

(52) U.S. Cl.
CPC ............... *G07F 17/322* (2013.01); *A61K 9/12* (2013.01); *A63F 11/0011* (2013.01); *G06F 17/3293* (2013.01); *A63F 1/12* (2013.01); *A61K 9/4866* (2013.01); *G07F 17/3286* (2013.01); *A61M 11/00* (2013.01); *A61K 9/2054* (2013.01); *A61K 9/2059* (2013.01); *A61M 11/005* (2013.01); *G07F 17/3211* (2013.01); *A63F 1/14* (2013.01)
USPC ................ 424/43; 128/200.14; 128/200.21

(58) Field of Classification Search
None
See application file for complete search history.

(56) References Cited

FOREIGN PATENT DOCUMENTS

WO 2004022132 3/2004

OTHER PUBLICATIONS

G Koster, C Lifshitz. "An electrospray ionization flow tube study of the protonated betaine/ammonia complex." International Journal of Mass Spectrometry, vol. 195/196, 2000, pp. 11-19.*
SM Berge, LD Bighley, DC Monkhouse. "Pharmaceutical Salts." Journal of Pharmaceutical Sciences, vol. 66 No. 1, Jan. 1977, pp. 1-19.*
Huntzicker,J.J.et al., "Neutralization of Sulfuric Acid Aerosol by Ammonia", Environ. Sci. Technol., 1980, vol. 14, No. 7, pp. 819-824.
Ito, K. et al., "A Continuous Monitoring System for Strong Acidity in Aerosols", Anal. Chem., 1998, vol. 70, No. 14, pp. 2839-2847.
Liggio, J et al., "Depression of Ammonia Uptake to Sulfuric Acid Aerosols by Competing Uptake of Ambient Organic Gases", Environ. Sci. Technol., Mar. 15, 2011, vol. 45, No. 7, pp. 2790-2796.
Swartz, E. et al., "Uptake of Gas-Phase Ammonia. 2. Uptake by Sulfuric Acid Surfaces", J. Phys. Chem. A 1999, vol. 103, No. 44, pp. 8824-8833.
International Search Report Form PCT/ISA/220, International Application No. PCT/US2012/067168, pp. 1-10, Dated Mar. 21, 2013.

* cited by examiner

*Primary Examiner* — Frederick Krass
*Assistant Examiner* — Isaac Shomer
(74) *Attorney, Agent, or Firm* — Blaine T. Bettinger; Bond Schoeneck & King, PLLC

(57) ABSTRACT

Systems and methods for neutralizing a solution comprising a compound of interest, comprising: aerosolizing a solution, wherein the solution is a low pH solution and comprises the compound of interest; contacting the aerosolized solution with ammonia vapor, wherein the ammonia vapor neutralizes at least a portion of said aerosolized solution; and removing at least some water from the neutralized aerosolized solution, wherein the neutralized aerosolized solution is at least partially dehydrated.

5 Claims, 4 Drawing Sheets

100 — Dissolve target of interest in low pH solution

110 — Place the low pH solution in the nebulizer

120 — Aerosolize solution, which travels through neutralization apparatus

130 — Generate ammonia vapor

140 — Inject ammonia vapor into the neutralization apparatus to neutralize aerosol stream 150 — Remove water from neutralized aerosol stream 160 — Inhale neutralized aerosol

FIG. 1

METHOD OF NEUTRALIZING AN AEROSOL CONTAINING A COMPOUND OF INTEREST DISSOLVED IN A LOW PH SOLUTION

CROSS-REFERENCE TO RELATED APPLICATIONS

This application claims priority to U.S. Provisional Patent Application Ser. No. 61/565,057, filed on Nov. 30, 2011 and entitled "Method of Neutralizing an Aerosol Containing a Compound of Interest Dissolved in a Low pH Solution," the entire disclosure of which is incorporated herein by reference.

BACKGROUND OF THE INVENTION

1. Field of the Invention

The present invention relates to methods of delivery of pharmaceuticals or drug candidates and, more specifically, to the use of ammonia to neutralize a low pH aerosol.

2. Description of the Related Art

Many active pharmaceutical ingredients ("APIs") or drug candidates ("DCs") have poor aqueous solubility. The solubility of the API or DC can be pH-dependent, and often the API or DC can only be dissolved in a low pH solution. The solubility can further depend on the particular acid used to lower the pH. For example, an API or DC may exhibit better solubility in p-toluene sulfonic acid compared to methanesulfonic acid or phosphoric acid. Other acids that are used to dissolve an API or DC include sulfuric acid and hydrochloric acid, among others.

Some APIs or DCs are designed to be delivered by inhalation as a treatment for a disease of the lung or to be absorbed through the lung to treat a systemic disease, among other uses. However, to deliver an API or DC by inhalation it first must be aerosolized. Aerosols can contain particles of various sizes, which may be varied in order to control delivery of the API to different parts and/or levels of the lung. Particle sizes can range from less than 100 nm to more than 5 microns.

There are many ways to aerosolize a compound. One such method is to aerosolize a liquid containing the API or DC dissolved in a solution. Devices that aerosolize liquid include jet nebulizers that use compressed air, such as the PARI nebulizer or the Medi-Nuclear nebulizer. Other devices use ultrasound to generate an aerosol. Still other devices use mechanical vibration or piezoelectric energy.

An API or DC dissolved in a low pH solution and aerosolized for delivery can cause inflammation and injury to the airways and lung if inhaled. Accordingly, there is a continued need to increase the pH of a low pH aerosol prior to inhalation.

BRIEF SUMMARY OF THE INVENTION

In accordance with the foregoing objects and advantages are described methods and systems for delivery of pharmaceuticals or drug candidates, and applications thereof.

According to one aspect, a method for neutralizing a solution comprising a compound of interest, the method comprising: (i) aerosolizing a solution, wherein the solution is a low pH solution and comprises the compound of interest; (ii) contacting the aerosolized solution with ammonia vapor, wherein the ammonia vapor neutralizes at least a portion of the aerosolized solution; and (iii) removing at least some water from the neutralized aerosolized solution, wherein the neutralized aerosolized solution is at least partially dehydrated.

According to a second aspect is the above method, further comprising the step of dissolving the compound of interest in the low pH solution.

According to a third aspect is the above method, further comprising the step of generating the ammonia vapor.

According to a fourth aspect is the above method, wherein the dehydrated neutralized aerosolized solution is inhaled.

According to a fifth aspect is the above method, further comprising the step of presenting the at least partially dehydrated neutralized aerosolized solution for inhalation.

According to a sixth aspect is the above method, wherein the low pH solution comprises an acid selected from the group consisting of: p-toluene sulfonic acid, methanesulfonic acid, phosphoric acid, sulfuric acid, hydrochloric acid, and combinations thereof.

According to another aspect, a method for neutralizing a solution comprising a compound of interest, the method comprising the steps of: (i) dissolving the compound of interest in a solution, wherein the solution is a low pH solution and comprises the compound of interest; (ii) aerosolizing the solution; (iii) generating an ammonia vapor; (iv) contacting the aerosolized solution with ammonia vapor, wherein the ammonia vapor neutralizes at least a portion of the aerosolized solution; (v) removing at least some water from the neutralized aerosolized solution, wherein the neutralized aerosolized solution is at least partially dehydrated; and (vi) presenting the at least partially dehydrated neutralized aerosolized solution for inhalation.

According to another aspect, a system for neutralizing a solution comprising a compound of interest, the system comprising: (i) a nebulizer module, wherein the nebulizer portion is adapted to aerosolize a solution, wherein the solution is a low pH solution and comprises the compound of interest; (ii) a contacting module, wherein the contacting module is adapted to allow the aerosolized solution to contact an ammonia vapor, wherein ammonia vapor neutralizes at least a portion of the aerosolized solution upon contact; and (iii) a dehydration module, wherein the dehydration module is adapted to remove at least some water from the neutralized aerosolized solution.

According to a second aspect is the above method, wherein further comprising a dissolving module, wherein the dissolving module is adapted to allow the compound of interest to be dissolved in the low pH solution.

According to third aspect is the above method, further comprising a generating module, wherein the generating module is adapted to generate the ammonia vapor.

According to fourth aspect is the above method, further comprising an inhalation module, wherein the inhalation module is adapted to allow inhalation of the dehydrated neutralized aerosolized solution is inhaled.

According to fifth aspect is the above method, wherein the low pH solution comprises an acid selected from the group consisting of: p-toluene sulfonic acid, methanesulfonic acid, phosphoric acid, sulfuric acid, hydrochloric acid, and combinations thereof.

According to sixth aspect is the above method, wherein the contacting module comprises an injection port adapted for injection of the ammonia vapor.

According to seventh aspect is the above method, further comprising a negative pressure source, wherein the vacuum source is adapted to pull the aerosolized solution through the system.

According to eighth aspect is the above method, wherein the negative pressure source is a vacuum.

According to ninth aspect is the above method, further comprising a negative pressure regulator.

According to tenth aspect is the above method, further comprising an animal restrainer adapted to encapsulate at least a portion of an animal.

According to eleventh aspect is the above method, wherein the dehydration module is a drying column.

According to twelfth aspect is the above method, wherein the drying column comprises one or more silica beads.

According to thirteenth aspect is the above method, further comprising a collection module, wherein the collection module is adapted to allow collection of the dehydrated neutralized aerosolized solution.

BRIEF DESCRIPTION OF THE SEVERAL VIEWS OF THE DRAWING(S)

The present invention will be more fully understood and appreciated by reading the following Detailed Description in conjunction with the accompanying drawings, in which:

FIG. 1 is a flowchart of one embodiment of a method of neutralizing a low pH solution containing an API, DC, or any other chemical entity;

DETAILED DESCRIPTION OF THE INVENTION

Figure 2:
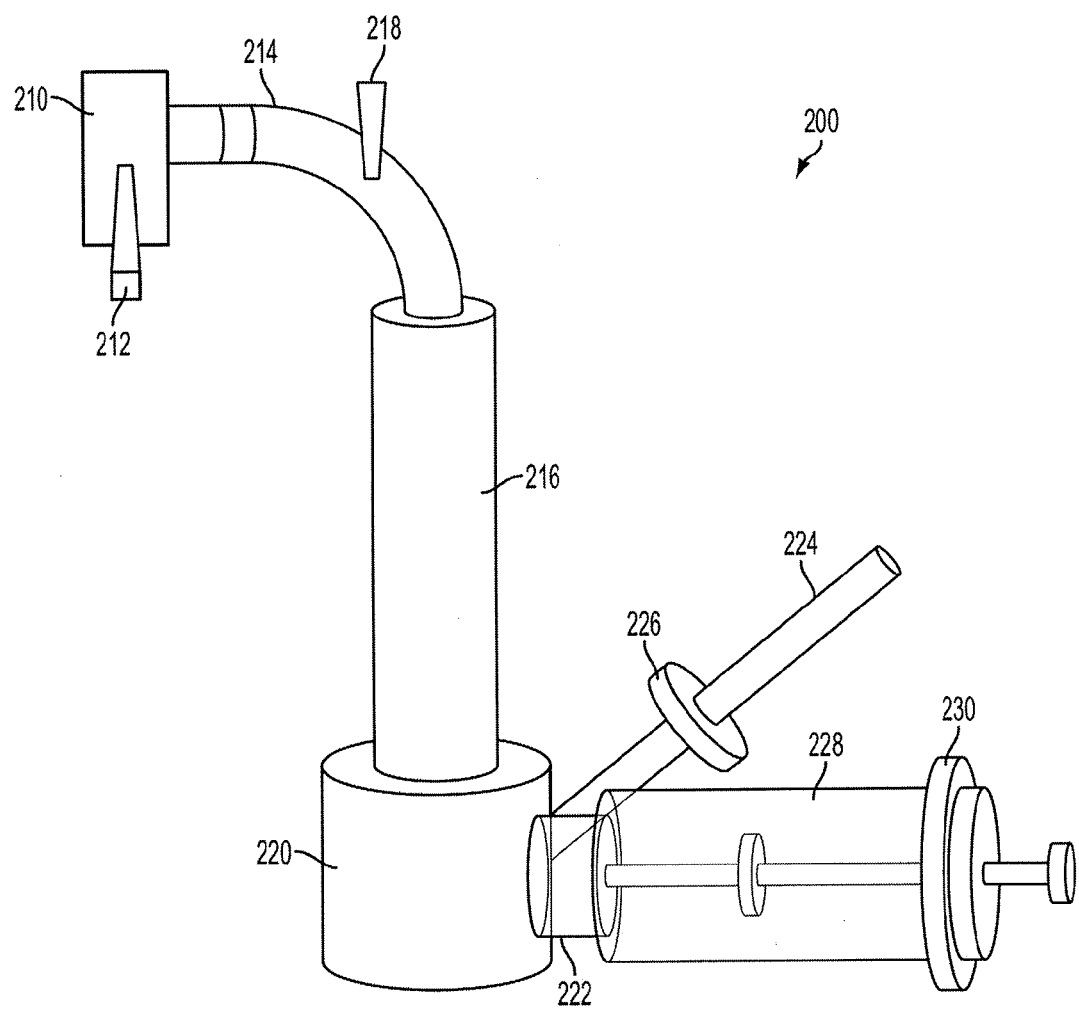
FIG. 2 is a schematic representation of an aerosol neutralizer apparatus according to one embodiment.

Referring now to the drawings, wherein like reference numerals refer to like parts throughout, there is seen in FIG. 1 a flowchart of one embodiment of a method of neutralizing a low pH solution containing an API, DC, or any other chemical entity. In one embodiment, the method is used to deliver a neutralized API or DC as a dry powder to research animals such as rats for purposes of drug testing. This method could be applied to any air-breathing animal, including mice, guinea pigs, rabbits, ferrets, dogs, and any other air-breathing laboratory research animal. In another embodiment, the method could be applied to a human being.

At step 100 of the method the target is dissolved in a low pH solution. The target of interest is, for example, an API or DC, and is often in the form of its free base. A low pH solution is a solution with a pH less than 1, or a solution with a pH in the range of 1-2, 2-3, or 3-4, among others. The solution can comprise, for example, p-toluene sulfonic acid, methanesulfonic acid, phosphoric acid, sulfuric acid, or hydrochloric acid, among many others. One of skill in the art would recognize that a wide variety and range of components could be used in the low pH solution.

At step 110, the low pH solution is placed in a nebulizer. At step 120, the solution is aerosolized by the nebulizer. Once aerosolized, the solution can be driven toward an ammonia vapor input, including, for example, being pulled by vacuum, among many other possible mechanisms. Ammonia vapor input can be generated at step 130 by, for example, bubbling air through a glass frit into a solution of ammonium hydroxide, or through one or more other possible mechanisms. The concentration of ammonium hydroxide can vary depending on the pH of the aerosol, the desired pH of the neutralized product, and a variety of other factors. In one embodiment, the concentration of ammonium hydroxide is 0.3%, although other concentrations are possible.

At step 140 of the method, the generated ammonia vapor is injected into the neutralization apparatus to neutralize the aerosol stream. The flow of the ammonia vapor into the system can be controlled by, for example, a flow meter. In one embodiment, the flow rate of the ammonia vapor is 0.3 liters/minute, although other flow rates are possible and can depend on a variety of factors including the pH of the input, the desired pH of the contents, and many other factors. The ammonia vapor flows into the aerosol stream at the determined rate, contacts particles of the target of interest, such as a DC dissolved in an aqueous acid solution, and neutralizes the particles.

At step 150, at least some of the water is removed from the neutralized aerosol stream. In one embodiment, the neutralized particles are driven through a drying column which removes water from the aerosol stream, resulting in an ammonium salt of the target of interest as a dry powder. Many other methods of removing at least some of the water are possible.

Finally, at step 160, the powder is inhaled. The powder can be inhaled directly, or can be further processed or altered, depending on the needs of the user and the designs of the system, among others.

FIG. 2 depicts an embodiment of an apparatus for performing one or more of the neutralization methods described herein. Although a neutralization method is described in terms of the embodiment depicted in FIG. 2, many other embodiments of an apparatus for performing one or more of the neutralization methods are possible. For example, the apparatus depicted in FIG. 2, or any other apparatus embodiment, could be miniaturized or made larger depending on the needs of the user and the designs of the system, among other factors.

As shown in FIG. 2, the device 200 comprises a nebulizer 210. The nebulizer can be a jet nebulizer connected to a source of compressed air 212, although other nebulizers or spray devices are known to those in the art and could be used according to the methods and systems described herein. Device 200 further comprises a tube 214 connecting the nebulizer to a drying column 216. Tube 214 also contains an injection port 218 for injection of ammonia and/or ammonia vapor into the system. Ammonia vapor can be generated, for example, by bubbling air through a glass frit into a solution of ammonium hydroxide, although other methods are possible. Generated ammonia vapor can then be injected into the neutralization apparatus via injection port 218 to neutralize the aerosol stream.

Figure 4:
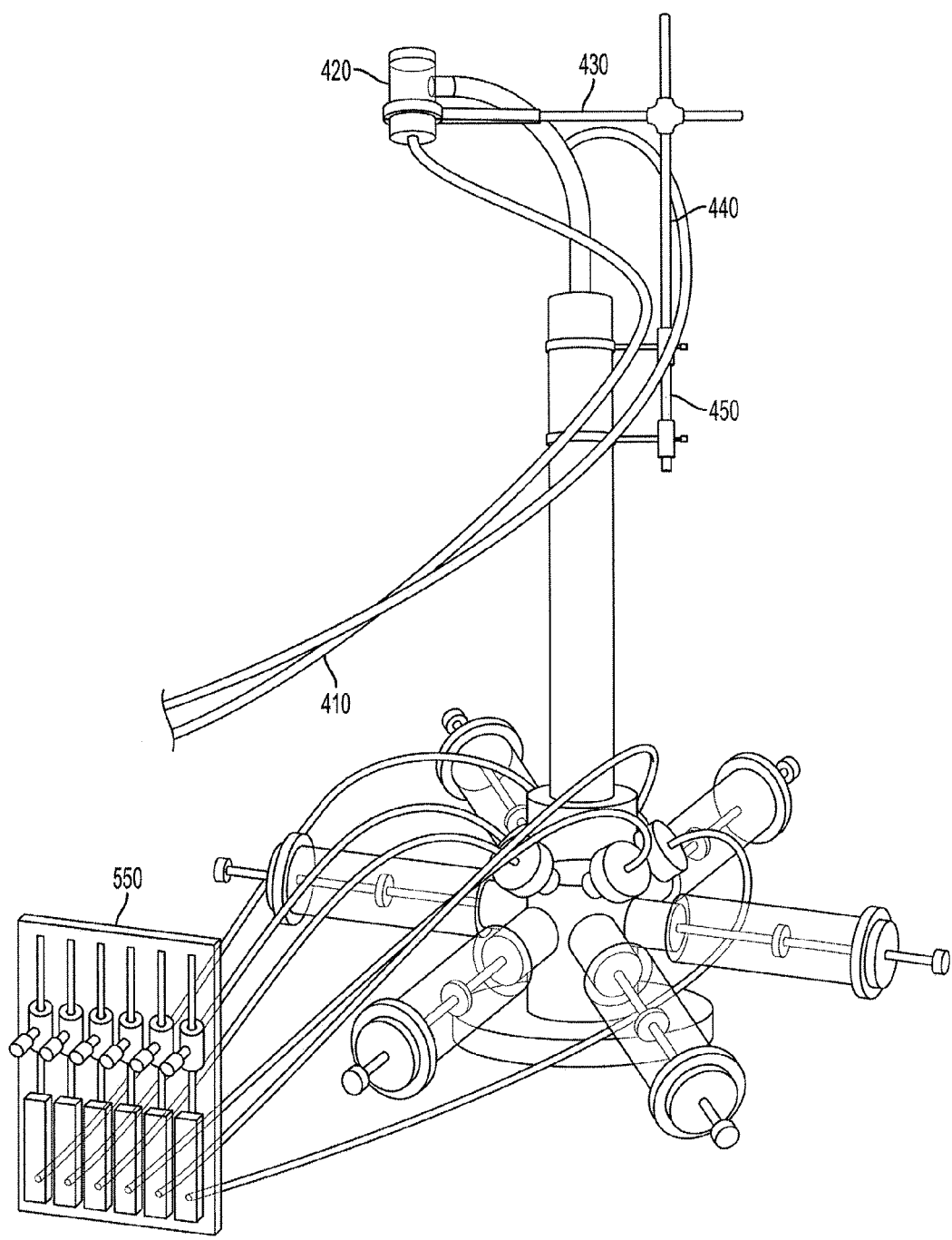
FIG. 4 is a view of an aerosol neutralizer apparatus according to one embodiment.

Drying column 216 can contain cartridges filled with silica beads that absorb water from aerosol particles, although many other methods of removing at least some of the water are possible. The drying column ends in exposure tower 220, which has one or more nosecones 222 with a hole for the vacuum source 224. While FIG. 2 depicts just one nosecone, many nosecones are possible to facilitate the method, as shown in FIG. 4. One or more flow regulators can be utilized to control the flow rate of the vacuum through the nosecone. Between the nosecone 222 and the vacuum source 224 is can be a filter 226. Filter 226 filters the dry powder aerosol and, according to one embodiment, collects the dry powder aerosol on a glass fiber filter which prevents the aerosol from clogging the vacuum flow regulators, and also allows collection of sample to determine the amount of aerosol containing particle per unit air, among other potential uses, including diagnostic functions.

Nosecone 222 terminates in an outlet for the neutralized dried aerosol. The outlet can be used for inhalation of the aerosol by a person or animal, or can be used to obtain aerosol for analysis and/or continued processing. In the embodiment shown in the figures, nosecone 222 terminates in an animal restrainer tube 228 and a restrainer tube cap 230. In this embodiment, the animal is inserted into the restrainer tube and the cap is fit over the end to encapsulate the animal. Once inside, neutralized dried aerosol is inhaled by the animal. The system can thus be used, for example, to study the inhalation efficiency and/or effects of the aerosolized API or DC on mammalian model organisms such as mice or rats, among many other uses. However, the animal restrainer tube 228 and/or restrainer tube cap 230 are not necessary to function of the method or system, and many other outlets or components can be attached to nosecone 222.

Figure 3:
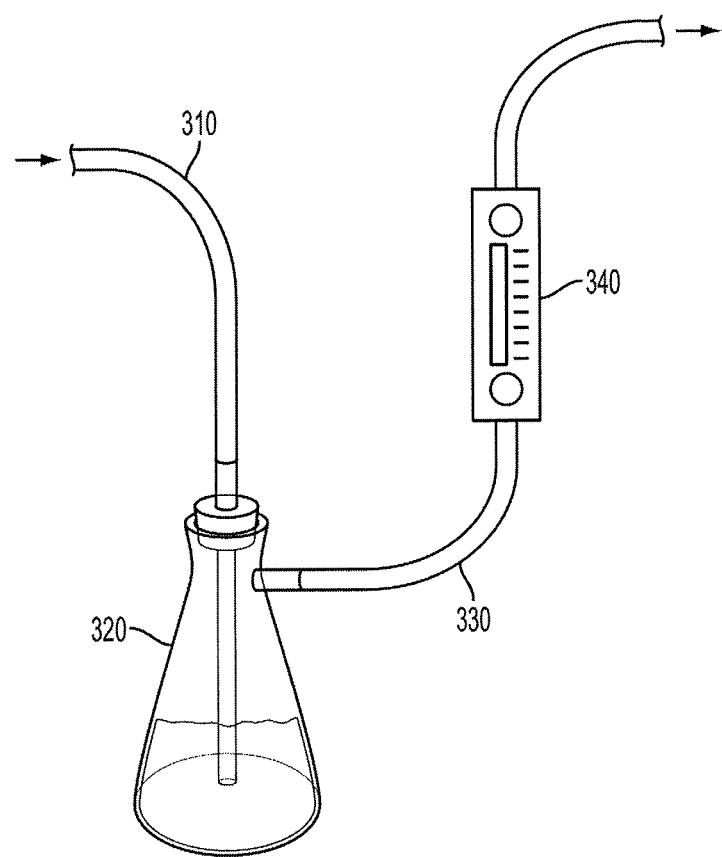
FIG. 3 is a view of an ammonia vapor generator according to one embodiment.

FIG. 3 is an image of an ammonia vapor source according to one embodiment. In this embodiment, compressed air flows into an Erlenmeyer flask at 310. At 320 is an Erlenmeyer flask containing a fritted glass tube and ammonium hydroxide solution. At this point, the air bubbles through the ammonium hydroxide solution, thereby generating ammonia vapor. At 330 is an ammonia vapor outlet. Finally, at 340 is a flow meter which optionally controls the flow rate of the generated ammonia vapor. Although a method of generating an ammonia or other vapor is shown in terms of FIG. 3, many other methods, mechanisms, and systems for generating an ammonia or other vapor are known and possible.

FIG. 4 is an image of an embodiment of an apparatus for performing a neutralization method as described herein. Although a neutralization method is described in terms of the embodiment depicted in FIG. 4, many other embodiments of an apparatus for performing one or more of the neutralization methods are possible. For example, the apparatus depicted in FIG. 4, or any other apparatus embodiment, could be miniaturized or made larger depending on the needs of the user and the designs of the system, among other factors.

At 420 in FIG. 4 is a compressed air source connected to a nebulizer. At 430 is a tube from the nebulizer to the drying column, at 440 is the injection port for ammonia vapor, and at 450 is the drying column. In this embodiment, the drying column contains cartridges loaded with silica beads, although many other means, mechanisms, systems, and methods of removing at least some water are possible. In this embodiment, the apparatus comprises numerous nosecones, although either more or fewer nosecones that the six depicted are possible. At 550 of the embodiment are one or more vacuum flow meters which regulate the vacuum for each nosecone.

According to further embodiments, the device can be miniaturized and adapted for multi-dose inhalations with a handheld device. According to one or more of these embodiments, the device or apparatus can be used to treat an illness or otherwise deliver an API or DC, among other things.

Although the present invention has been described in connection with a preferred embodiment, it should be understood that modifications, alterations, and additions can be made to the invention without departing from the scope of the invention as defined by the claims.

What is claimed is:

1. A method for neutralizing a solution comprising an active pharmaceutical ingredient (API) or drug candidate (DC), the method comprising the steps of:
   aerosolizing a solution, wherein said solution is a low pH solution and comprises the API or DC;
   contacting the aerosolized solution with ammonia vapor, wherein said ammonia vapor neutralizes at least a portion of said aerosolized solution; and
   removing at least some water from the neutralized aerosolized solution, wherein said neutralized aerosolized solution is at least partially dehydrated; and then delivering the at least partially dehydrated neutralized aerosolized solution to a human being or air-breathing animal by inhalation.

2. The method of claim 1, further comprising the step of dissolving the API or DC in the low pH solution.

3. The method of claim 1, further comprising the step of generating said ammonia vapor.

4. The method of claim 1, wherein the low pH solution comprises an acid selected from the group consisting of: p-toluene sulfonic acid, methanesulfonic acid, phosphoric acid, sulfuric acid, hydrocholoric acid, and combinations thereof.

5. A method for neutralizing a solution comprising an active pharmaceutical ingredient (API) or drug candidate (DC), the method comprising the steps of:
   dissolving the API or DC in a solution, wherein said solution is a low pH solution and comprises the API or DC;
   aerosolizing the solution;
   generating an ammonia vapor;
   contacting the aerosolized solution with ammonia vapor, wherein said ammonia vapor neutralizes at least a portion of said aerosolized solution;
   removing at least some water from the neutralized aerosolized solution, wherein said neutralized aerosolized solution is at least partially dehydrated; and
   then delivering the at least partially dehydrated neutralized aerosolized solution to a human being or air-breathing animal by inhalation.

* * * * *